(12) United States Patent
Bruessow et al.

(10) Patent No.: US 6,998,119 B1
(45) Date of Patent: Feb. 14, 2006

(54) **FEED COMPOSITION CONTAINING *BIFIDOBACTERIUM* CNCM 1-2168 CAPABLE OF PREVENTING DIARRHEA**

(75) Inventors: Harald Bruessow, La Tour-de Peilz (CH); Roberto Reniero, Le Mont-Pelerin (CH); Josette Sidoti, Paudex (CH)

(73) Assignee: Nestec S.A., Vevey (CH)

( * ) Notice: Subject to any disclaimer, the term of this patent is extended or adjusted under 35 U.S.C. 154(b) by 260 days.

(21) Appl. No.: 10/049,368

(22) PCT Filed: Jul. 26, 2000

(86) PCT No.: PCT/EP00/07207

§ 371 (c)(1),
(2), (4) Date: May 9, 2002

(87) PCT Pub. No.: WO01/10453

PCT Pub. Date: Feb. 15, 2001

(30) Foreign Application Priority Data

Aug. 5, 1999 (EP) .................................. 99115501

(51) Int. Cl.
*C12N 1/00* (2006.01)
*C12N 1/20* (2006.01)

(52) U.S. Cl. .................. 424/93.4; 424/439; 435/252.1; 435/822

(58) Field of Classification Search ............. 435/252.1, 435/822; 424/93.1, 93.4, 439
See application file for complete search history.

(56) References Cited

U.S. PATENT DOCUMENTS

| | | | |
|---|---|---|---|
| 5,902,578 A | | 5/1999 | Halpin-Dohnalek |
| 6,060,050 A | * | 5/2000 | Brown et al. .............. 424/93.3 |

FOREIGN PATENT DOCUMENTS

| | | |
|---|---|---|
| EP | 0 768 375 A1 | 4/1997 |
| EP | 0577903 B1 | 12/1997 |
| EP | 0 904 784 A1 | 3/1999 |
| WO | WO 97/00078 | 6/1996 |

OTHER PUBLICATIONS

XP-002137052, Pharmaceutical Probiotics for the Treatment of Anaerobic and Other Infections; McFarland et al, Anaerobe, vol. 3, pp. 74-78 (1997).

XP-000978813, Interactions Mediating Bacterial Translocation in the Immature Intestine, Duffy, V. 130, pp. 4325-4365 (2000).

B.J.B. Wood and W.H. Holzapfel, *"The Genus Bifidobacterium": "Genera of Lactic Acid Bacteria"*, Blackie A&P, pp. 279-306 (1995).

* cited by examiner

*Primary Examiner*—David M. Naff
*Assistant Examiner*—Deborah K. Ware
(74) *Attorney, Agent, or Firm*—Bell, Boyd & Lloyd LLC

(57) ABSTRACT

The present invention pertains to the use of microorganisms belonging to the genus *Bifidobacterium* for preparing a carrier for the treatment or prophylaxis of diarrhea. The invention also relates to food or pharmaceutical compositions containing such microorganisms.

4 Claims, 1 Drawing Sheet

FEED COMPOSITION CONTAINING *BIFIDOBACTERIUM* CNCM 1-2168 CAPABLE OF PREVENTING DIARRHEA

BACKGROUND OF THE INVENTION

The present invention pertains to the use of non-pathogenic microorganisms of the genus *Bifidobacterium* for preparing a carrier for the treatment or prophylaxis of diarrhea brought about by rotaviruses, and to food or pharmaceutical compositions containing such microorganisms.

Organisms that produce lactic acid as a major metabolic component have been known for a long time. These bacteria may be found in milk or in milk processing factories, respectively, living or decaying plants but also in the intestine of man and animals. These microorganisms, summarized under the term "lactic acid bacteria", represent a rather inhomogeneous group and comprise e.g. the genera *Lactococcus, Lactobacillus, Streptococcus, Bifidobacterium, Pediococcus* etc.

Lactic acid bacteria have been utilized as fermenting agents for the preservations of food taking benefit of a low pH and the action of fermentation products generated during the fermentative activity thereof to inhibit the growth of spoilage bacteria. In addition, lactic acid bacteria have also been used for preparing from milk a variety of different foodstuff such as cheese, yogurt and other fermented dairy products.

Quite recently, lactic acid bacteria have attracted a great deal of attention in that some strains have been found to exhibit valuable properties to man and animals upon ingestion. In particular, specific strains of *Lactobacillus* or *Bifidobacterium* have been found to be able to colonize the intestinal mucosa and to assist in the maintenance of the well-being of man and animal.

In this respect, EP 0 768 375 discloses specific strains of the genus *Bifidobacterium*, that are capable to become implanted in the intestinal flora and may adhere to intestinal cells. These Bifidobacteria are reported to assist in immunomodulation, being capable to competitively exclude adhesion of pathogenic bacteria to intestinal cells, thus assisting in the maintenance of the individual's health.

During the last few years research has also focused on the potential use of lactic acid bacteria as probiotic agents. Probiotics are considered to be viable microbial preparations which promote the individual's health by preserving the natural microflora in the intestine. A microbial preparation may be commonly accepted as a probiotic in case the effectual microbes thereof and their mode of action are known. Probiotics are deemed to attach to the intestine's mucosa, colonize the intestinal tract and likewise prevent attachment of harmful microorganisms thereon. A crucial prerequisite for their action resides in that they have to reach the gut's mucosa in a proper and viable form and do not get destroyed in the upper part of the gastrointestinal tract, especially by the influence of the low pH prevailing in the stomach.

In this respect, WO 97/00078 discloses a specific strain, termed *Lactobacillus* GG (ATCC 53103), as such a probiotic. The microorganism is particularly employed in a method of preventing or treating food induced hypersensitivity reactions in that it is administered to a recipient together with a food material that has been subjected to a hydrolysis treatment with pepsin and/or trypsin. The *Lactobacillus* strain selected is described as exhibiting adhesive and colonizing properties and showing a protease enzyme system, so that the protein material contained in the foodstuff to be administered is further hydrolysed by means of proteases secreted by the specific *Lactobacillus* strain. The method discussed in this document shall eventually result in the uptake of protein material by the gut that does not show a substantial amount of allergenic material anymore.

Further, in EP 0 577 903 reference is made to the use of such lactic acid bacteria having the ability of replacing *Heliobacter pylori*, the acknowledged cause for the development of ulcer, in the preparation of a support intended for the therapeutic or prophylactic treatment of an ulcer associated with the action of *Heliobacter pylori*.

In view of the valuable properties particular strains of lactic acid bacteria may exhibit there is a desire in the art to find additional properties of bacterial strains beneficial to the well being of man and/or animal.

A need, therefore, exists to provide additional lactic acid bacteria that may exert beneficial activities to living beings upon ingestion.

SUMMARY OF THE INVENTION

In the course of the studies leading to the invention it was now surprisingly found that microorganisms of the genus *Bifidobacterium* show properties not yet recognized in the art. In effect, the present invention provides for the use of microorganisms belonging to the genus *Bifidobacterium* and being capable to essentially prevent infection of intestinal cells by rotaviruses for the preparation of a carrier for the treatment or prophylaxis of diarrhea.

In an embodiment, the Bifidobacteria to be used are preferably selected from the group consisting of *Bifidobacterium* adolescentis or *Bifidobacterium longum*, preferably *Bifidobacterium* adolescentis, and is more preferably *Bifidobacterium* CNCM 1-2168.

The microorganisms may be used for the preparation of a variety of ingestable carriers, such as e.g. milk, yogurt, curd, fermented milks, milk based fermented products, fermented cereal based products, milk based powders, infant formulae or pet food and may be included in the respective carrier in an amount of from about $10^5$ cfu/g to about $10^{11}$ cfu/g. For the purpose of the present invention the abbreviation cfu shall designate a "colony forming unit" that is defined as number of bacterial cells as revealed by microbiological counts on agar plates.

In an embodiment, the present invention also provides for a food or pharmaceutical composition containing at least one of the *Bifidobacterium* strains capable to essentially prevent infection of intestinal cells by rotaviruses.

For preparing a food composition according to the present invention at least one of the *Bifidobacterium* strains used according to the present invention is incorporated in a suitable support, in an amount of from about $10^5$ cfu/g to about $10^{11}$ cfu/g, preferably from about $10^6$ cfu/g to about $10^{10}$ cfu/g, more preferably from about $10^7$ cfu/g to about $10^9$ cfu/g.

In case of a pharmaceutical preparation the product may be prepared in form of tablets, liquid bacterial suspensions, dried oral supplements, wet oral supplements, dry tube feeding or a wet tube feeding etc., with the amount of *Bifidobacterium* strains to be incorporated therein being in the range of up to $10^{12}$ cfu/g, preferably from about $10^7$ cfu/g to about $10^{11}$ cfu/g, more preferably from about $10^7$ cfu/g to about $10^{10}$ cfu/g.

The microorganisms may further be formulated in the carrier so as to obtain a desired release pattern, such as encapsulation etc. Based upon the desired objective the person skilled in the art will select the appropriate excipients and/or additives.

The activity of the microorganisms in the individual's intestine is of course dose dependent. That is, the more the microorganisms are incorporated by means of ingesting the above food material or the pharmaceutical composition, respectively, the higher the protective and/or curing activity thereof. Since the used microorganisms are not detrimental to mankind and animals and have eventually been isolated from a natural surrounding, namely baby feces, a high amount thereof may be incorporated so that essentially a high proportion of the individual's intestine will be colonized by the microorganisms.

Additional features and advantages of the present invention are described in, and will be apparent from the following Detailed Description of the Invention and the figures.

DETAILED DESCRIPTION OF THE INVENTION

Figure 1:
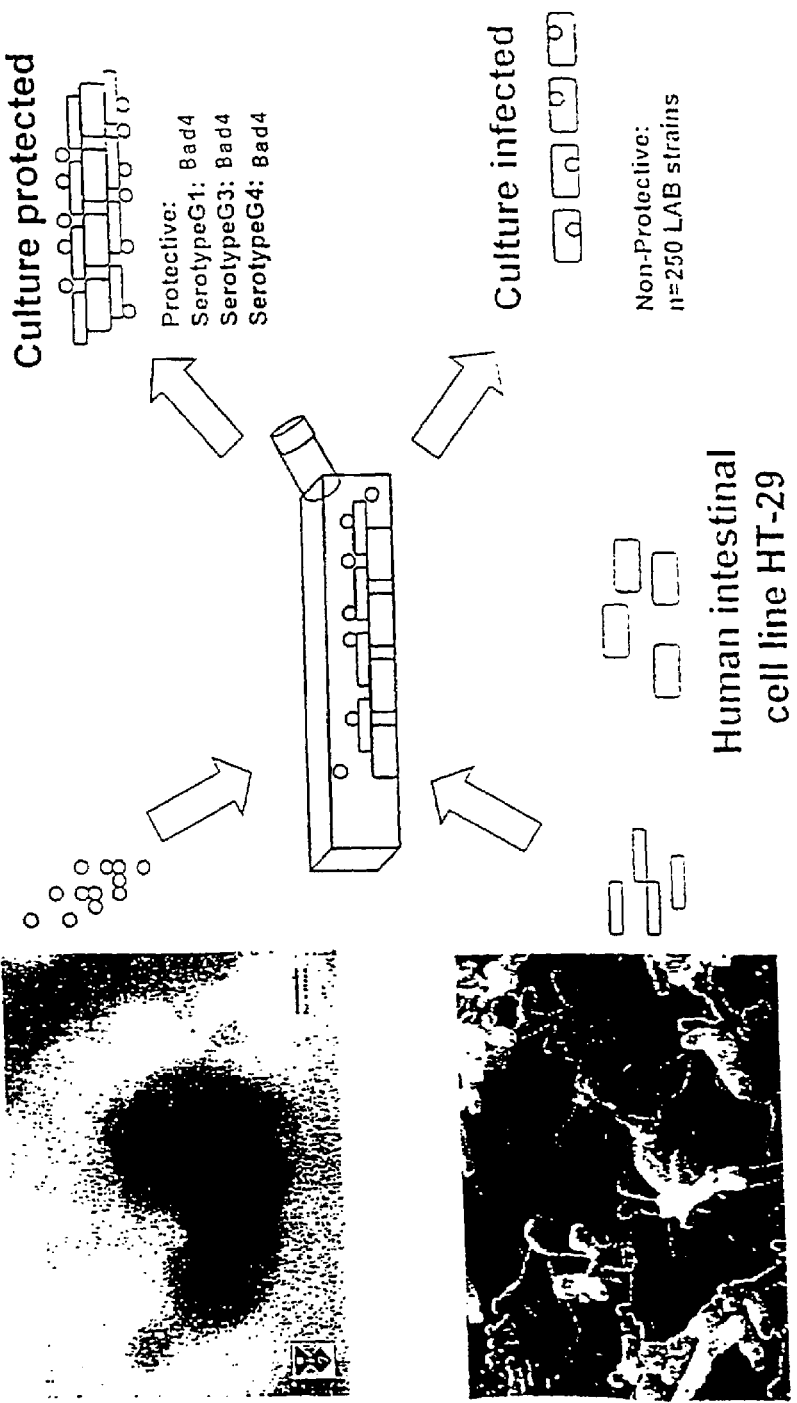
FIG. 1 shows a scheme illustrating the cell culture screening for assessing rotaviral protective properties of bacterial strains.

During the extensive studies leading to the present invention the inventors have investigated different bacterial strains isolated from baby feces or obtained from the American Tissue and Cell Collection (ATCC 15704). The different strains were examined for their capability to prevent infection of intestinal cells with rotaviruses that are known to cause diarrhea.

Several bacterial genera comprising *Bifidobacterium, Lactococcus, Streptococcus* were screened for their rotavirus inhibitory properties. The tests for the inhibitory property were essentially performed with three rotavirus serotypes representing the major etiological agents of human viral diarrhea (serotypes G1, G3 and G4).

The various lactic acid bacteria were grown in a suitable medium, such as MRS, Hugo-Jago or M17 medium at temperatures of from about 30 to 40° C. corresponding to their optimal growth temperature. After reaching stationary growth the bacteria were collected by centrifugation and re-suspended in physiological NaCl solution. Between the different tests the bacterial cells were stored frozen (−20° C.).

The various rotavirus stocks were prepared by infection of confluent cell monolayers. The rotaviruses were incubated before infection. The cells were infected with 20 tissue culture infectious doses.

For assessing anti-rotaviral properties two different protocols were applied. According to one protocol the various bacterial strains were examined for their direct interaction with the rotavirus strain while in the second protocol the bacteria were screened for those strains that interact with cellular rotavirus receptors.

The first protocol involved contacting the respective bacterial suspension each with a different rotavirus strain and incubating in suitable media. Subsequently, the virus-bacteria mixture was applied to a monolayer of cells of the human undifferentiated colon adenoma cells HT-29 (intestinal epithelial cell line) and incubation was continued. Virus replication was then assayed.

The second protocol involved incubating the respective bacterial suspension first together with a monolayer of cells of the human undifferentiated colon adenoma cells HT-29 and adding the virus subsequently. After continued incubation virus replication was assayed.

Rotavirus replication may easily be assessed by histo-immunological staining of rotavirus proteins in infected cells.

A rotavirus inhibitory effect was attributed to a given bacterium when the number of infected cells was reduced by 90% in the cell culture inoculated with rotavirus plus the indicated bacteria in comparison with cells inoculated only with rotavirus.

Out of a total of 260 different bacterial strains primarily isolated merely 4 could be shown to essentially inhibit rotaviral replication. The different bacteria were ascertained to belong to the genus *Bifidobacterium* subspecies *adolescentis* or *longum*. One strain belonging to the species *Bifidobacterium* adolescentis, which has been termed Bad4, has been deposited in accordance with the Budapest Treaty and has received the deposit number CNCM I-2168. This strain proved to be extremely effective in preventing infection of human cells by rotaviruses.

The present invention will now be described by way of example and not limitation.

Media and Solutions:

MRS (Difco),

Hugo-Jago (Tryptone Difco 30 g/l, Yeast Extract Difco 10 g/l, Lactose Difco 5 g/l , $KH_2PO_4$ 5 g/l, Beef Extract Difco 2 g/l, agar Difco 2 g/l)

M17 (Difco)

M199 (Seromed)

Ringer solution (Oxoid)

PBS (NaCl 8 g/l, KCl 0.2 g/l, $Na_2HPO_4$ 1.15 µl, $KH_2PO_4$ 0.2 g/l))

Tryptose phosphate broth (Flow)

Trypsin-EDTA solution (Seromed)

Human rotavirus Wa (G1 serotype) and simian rotavirus SA-11 (G3 serotype) were obtained from P.A. Offit, Children's Hospital of Philadelphia, U.S.A. The DS-1×RRV reassortant virus was obtained from A. Kapikian, NIH Bethesda, U.S.A. The serotype 4 human rotavirus Hochi was obtained from P. Bachmann, University of Munich, Germany.

EXAMPLE 1

Isolation of Lactic Acid Bacteria from Baby Feces

Fresh feces were harvested from diapers of 16 healthy babies 15 to 27 days old. 1 g of fresh feces was placed under anaerobic conditions for transportation to the laboratory and microbiological analyses were run within 2 hours from sampling by serial dilutions in Ringer solution and plating on selective media. MRS agar plus antibiotics (phosphomycine 80 µg/ml, sulfamethoxazole 93 µg/ml, trimethoprime 5 µg/ml) incubated at 37° C. for 48 hours was used to isolate lactic acid bacteria. Colonies were randomly picked up and purified. Physiological and genetic characterisation was performed on the isolates. In the tests another strain obtained from ATCC (ATCC 15704) was also used, which corresponds to the preferred strain Bad4 to be used according to the present invention.

EXAMPLE 2

Testing of Strains in Cell Culture for Anti-Rotaviral Activity

Several bacterial genera comprising *Bifidobacterium*, *Lactococcus* and *Streptococcus* were selected and tested for members which showed anti-rotaviral activity in the cell culture inhibition test (see below $1^{st}$ and $2^{nd}$ protocol). The genus *Lactococcus* was represented by a single species (*Lc. lactis*) consisting of two subspecies (*Lc. lactis* supsp. *lactis* and *cremoris*). A total of 30 strains were tested. The *Streptococcus* genus was represented by a single species (*S. thermophilus*) with 45 strains. The *Leuconostoc* and *Propionibacterium* genus were only represented by a single species (6 strains), while the *Enterococcus* and *Staphylococcus* genus was represented by two species each and a total of 17 strains.

In total, 260 bacterial strains were tested for rotavirus inhibitory activity.

$1^{st}$ Protocol:

30 μl of the respective bacterial suspension (containing on average $3 \times 10^6$ bacteria) were mixed with 70 μM199 medium supplemented with 10% tryptose phosphate broth (Flow) and 5% trypsin-EDTA solution (Seromed) to which were added 100 μl of virus in supplemented M199 medium. The virus-bacteria mixture thus obtained was incubated for 1 hour at 4° C. and for 1 hour at 37° C. Separately, cells of the human undifferentiated colon adenoma cells HT-29 growing as a confluent monolayer in 96-well microtiter plates (in M199 medium supplemented with 10% tryptose phosphate broth (Flow) and 5% trypsin- EDTA solution (Seromed) 1:4 diluted with PBS) were washed three times with phosphate-buffered saline (PBS ; pH 7.2). The virus-bacteria mixture processed as indicated above was transferred to the cells and the microtiter plates were incubated for 18 h in a $CO_2$ incubator (Heraeus). Virus replication was assayed as described below.

$2^{nd}$ Protocol:

30 μl of the bacterial suspension (supra) were mixed with 70 μl M199 medium supplemented with 10% tryptose phosphate broth (Flow) and 5% trypsin-EDTA solution (Seromed) and applied directly on HT-29 cells grown and pretreated as described in the $1^{st}$ protocol in the microtiter plates. After one hour incubation at 37° C. 100 μl of virus in supplemented M199 medium were added to the cells in the microtiter plates. The incubation was continued for 18 h in a $CO_2$ incubator (Heraeus). Virus replication was assayed as described below.

The rotavirus replication was assessed by histo-immunological staining of rotavirus proteins in infected cells as described hereafter.

One day after infection, the cell culture medium was removed from the microtiter plates and the cells were fixed with absolute ethanol for 10 min. Ethanol was discarded, and the plates were washed three times in PBS buffer. Then 50 μl of an anti-rotavirus serum (mainly directed against VP6 protein), produced in rabbits (obtained from the ISREC University of Lausanne) and diluted 1:2000 in PBS was added to each well and incubated for 1 h at 37° C. with a cover slip to prevent desiccation of the wells. The anti-serum was discarded afterwards and the plates were washed three times with PBS. Then 50 μl of anti-rabbit immunoglobulin G (IgG) antiserum produced in goats and coupled to peroxidase (GAR-IgG-PO; Nordic) were added at a dilution of 1:500 in PBS to each well and the plates were incubated for 1 hour at 37° C. The serum was discarded and the plates were again washed three times with PBS. Then 100 μl of the following substrate mixture was added to each well: 10 ml of 0.05 M Tris-hydrochloride (pH 7.8), 1 ml of $H_2O_2$ (30% suprapur, diluted 1:600 in $H_2O$; Merck) and 200 μl of 3-amino-9-ethylcarbazole (0.1 g/10 ml of ethanol stored in 200 μl aliquots at −80° C.; A-5754; Sigma). The plates were incubated for at least 30 min at room temperature. The substrate was discarded and the wells were filled with 200 μl of $H_2O$ to stop the reaction. Infected cell foci were counted with an inverted microscope (Diavert; Leitz).

Only very few bacterial strains interacted with rotaviruses. Merely 4 out of the 260 bacterial cells primarily selected inhibited rotavirus replication in at least one protocol. *Bifidobacterium* adolescentis CNCM I-2168 (Bad4) showed an extremely high activity against Serotype 1 Rotavirus, Serotype 3 rotavirus SA-11 and Serotype 4 rotavirus Hochi.

Bad4 is gram positive and catalase negative, it does not produce $CO_2$ during fermentation and produces just L (+) lactic acid according to methods disclosed in the "Genera of lactic acid bacteria", Ed. B. J. B. Wood and W. H. Holzapfel, Blackie A&P.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A food composition comprising a *Bifidobacterium* strain capable of preventing infection of intestinal cells of a mammal due to a rotavirus, wherein the *Bifidobacterium* strain is *Bifidobacterium* CNCM I-2168.

2. The food composition according to claim 1 wherein the food composition is selected from the group consisting of milk, yogurt, curd, cheese, fermented milk, milk based fermented products, ice-creams, fermented cereal based products, milk based powders, infant formula and pet food.

3. The food composition according to claim 1 wherein the food composition includes about $10^{11}$ cfu/g or less of the *Bifidobacterium* strain.

4. The food composition according to claim 1 wherein the food composition includes about $10^5$ cfu/g to about $10^{11}$ cfu/g of the *Bifidobacterium* strain.

* * * * *